(12) United States Patent
Perkins et al.

(10) Patent No.: US 10,274,366 B2
(45) Date of Patent: Apr. 30, 2019

(54) TUNGSTEN-HALOGEN ELECTROMAGNETIC RADIATION OPTICAL SYSTEMS SOURCE

(71) Applicant: Halliburton Energy Services, Inc., Houston, TX (US)

(72) Inventors: David L. Perkins, The Woodlands, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/308,044

(22) PCT Filed: Jun. 9, 2014

(86) PCT No.: PCT/US2014/041575
§ 371 (c)(1),
(2) Date: Oct. 31, 2016

(87) PCT Pub. No.: WO2015/191031
PCT Pub. Date: Dec. 17, 2015

(65) Prior Publication Data
US 2017/0052067 A1    Feb. 23, 2017

(51) Int. Cl.
*G01J 3/10* (2006.01)
*H01K 1/28* (2006.01)
*H01K 1/32* (2006.01)
*H01K 1/50* (2006.01)
*H01K 7/00* (2006.01)
(Continued)

(52) U.S. Cl.
CPC .............. *G01J 3/10* (2013.01); *G01N 21/255* (2013.01); *G01N 33/24* (2013.01); *H01K 1/28* (2013.01); *H01K 1/50* (2013.01); *H01K 1/32* (2013.01); *H01K 7/00* (2013.01); *Y02B 20/12* (2013.01)

(58) Field of Classification Search
None
See application file for complete search history.

(56) References Cited

U.S. PATENT DOCUMENTS 3,311,777 A * 3/1967 Schroder .................. H01K 1/54
313/315
5,508,587 A    4/1996 Williams et al.
(Continued)

FOREIGN PATENT DOCUMENTS

EP    0215524 A1    3/1987
JP    2000133202 A    5/2000
WO    2014042642 A1    3/2014

OTHER PUBLICATIONS

International Search Report dated Oct. 15, 2014; International PCT Application No. PCT/US14/41515.
(Continued)

*Primary Examiner* — Shawn Decenzo
(74) *Attorney, Agent, or Firm* — McGuireWoods LLP

(57) ABSTRACT

A tungsten-halogen electromagnetic radiation source has a sealed transparent aluminum oxynitride envelope defining an interior volume. At least one optical element is integrally formed into the aluminum oxynitride envelope. A tungsten filament is located in the aluminum oxynitride envelope. A fill gas in the interior volume contains at least a gaseous halogen compound.

20 Claims, 6 Drawing Sheets

(51) Int. Cl.
    *G01N 21/25*    (2006.01)
    *G01N 33/24*    (2006.01)

(56) References Cited

U.S. PATENT DOCUMENTS

| | | | | |
|---|---|---|---|---|
| 5,886,466 A * | 3/1999 | Bell | ......................... | H01K 1/50 |
| | | | | 313/569 |
| 6,956,328 B1 * | 10/2005 | Yu | ........................... | H01K 1/50 |
| | | | | 313/548 |
| 2005/0212432 A1 * | 9/2005 | Neil | ....................... | H01K 3/20 |
| | | | | 313/623 |
| 2006/0274529 A1 | 12/2006 | Cao | | |
| 2007/0018580 A1 | 1/2007 | Kupper et al. | | |
| 2008/0122361 A1 * | 5/2008 | Lapatovich | .......... | H01J 61/025 |
| | | | | 313/634 |
| 2009/0175043 A1 | 7/2009 | Frick | | |
| 2015/0247950 A1 * | 9/2015 | Perkins | ................ | G01J 3/0291 |
| | | | | 250/254 |

OTHER PUBLICATIONS

European Extended Search Report dated Nov. 3, 2017; European Patent Application No. 14894301.2.

\* cited by examiner

TUNGSTEN-HALOGEN ELECTROMAGNETIC RADIATION OPTICAL SYSTEMS SOURCE

The present disclosure relates generally to a spectroscopic electromagnetic radiation source, and more specifically to a tungsten-halogen electromagnetic radiation source having improved operating characteristics for use in spectroscopic measurement systems.

Incandescent electromagnetic radiation sources, including older versions with tungsten and carbon filaments and the newer, more advanced tungsten-halogen electromagnetic radiation sources, have been successfully employed as a highly reliable electromagnetic radiation source in optical spectroscopy for many decades. Tungsten electromagnetic radiation sources are relatively inexpensive and are easily replaced. Tungsten-halogen electromagnetic radiation sources generate a continuum of electromagnetic radiation beginning from the visible wavelengths to the infrared wavelengths. Most of the energy emitted by these electromagnetic radiation sources is dissipated as heat in the infrared wavelengths. Quartz envelopes, commonly used in tungsten-halogen electromagnetic radiation sources, have a spectral transmission curve that falls off susbstantially at wavelengths over 2800 nm.

BRIEF DESCRIPTION OF THE DRAWINGS

A better understanding of the present invention can be obtained when the following detailed description of example embodiments are considered in conjunction with the following drawings, in which.

DETAILED DESCRIPTION

Figure 1:
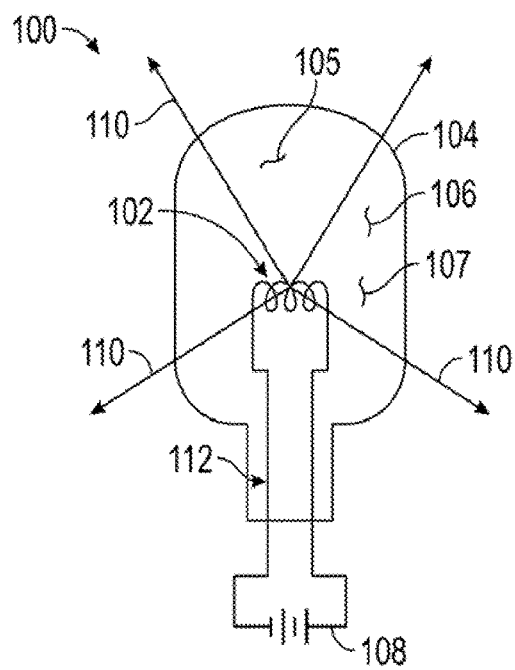
FIG. 1 shows a schematic representation of one example of a tungsten-halogen electromagnetic radiation source in accordance with aspects of the present disclosure.

As used herein, the terms "electromagnetic radiation source" and "lamp" are used interchangeably.

As used herein, the term "optical computing device" refers to an optical device that is configured to receive an input of electromagnetic radiation associated with a substance, such as a fluid, and produce an output of electromagnetic radiation from a processing element arranged within the optical computing device. The processing element may be, for example, an integrated computational element (ICE) used in the optical computing device. An ICE may comprise a multilayered optical thin-film interference based device that is designed to transmit a predetermined target spectrum. The target transmission spectrum may be indicative of a characteristic of interest of a fluid sample. The electromagnetic radiation that optically interacts with the processing element is changed so as to be readable by a radiation transducer, such that an output of the radiation transducer, usually in the form of an electrical voltage or current, can be related to a characteristic of the fluid. The input to, or output of, electromagnetic radiation to and/or from, the processing element can be reflected electromagnetic radiation, transmitted electromagnetic radiation, and/or dispersed electromagnetic radiation. Whether the radiation transducer analyzes reflected, transmitted, or dispersed electromagnetic radiation may be dictated by the structural parameters of the optical computing device as well as other considerations known to those skilled in the art. In addition, emission and/or scattering of the fluid, or a phase thereof, for example via fluorescence, luminescence, Raman, Mie, and/or Raleigh scattering, can also be monitored by the optical computing devices.

As used herein, the term "fluid" refers to any substance that is capable of flowing, including particulate solids, liquids, gases, slurries, emulsions, powders, muds, glasses, mixtures, combinations thereof, and the like. The fluid may be a single phase or a multiphase fluid. In some embodiments, the fluid can be an aqueous fluid, including water, brines, or the like. In other embodiments, the fluid may be a non-aqueous fluid, including organic compounds, more specifically, hydrocarbons, oil, a refined component of oil, petrochemical products, and the like. In some embodiments, the fluid can be acids, surfactants, biocides, bleaches, corrosion inhibitors, foamers and foaming agents, breakers, scavengers, stabilizers, clarifiers, detergents, a treatment fluid, fracturing fluid, a formation fluid, or any oilfield fluid, chemical, or substance as found in the oil and gas industry and generally known to those skilled in the art. The fluid may also have one or more solids or solid particulate substances entrained therein. For instance, fluids can include various flowable mixtures of solids, liquids and/or gases. Illustrative gases that can be considered fluids according to the present embodiments, include, for example, air, nitrogen, carbon dioxide, argon, helium, methane, ethane, butane, and other hydrocarbon gases, hydrogen sulfide, combinations thereof, and/or the like.

As used herein, the term "characteristic" refers to a chemical, mechanical, or physical property of a substance and may be used herein interchangeably with the phrase "analyte of interest." Illustrative characteristics of a substance that can be monitored with the optical computing devices disclosed herein can include, for example, chemical composition (identity and concentration, in total or of individual components), impurity content, pH, viscosity, density, ionic strength, total dissolved solids, salt content, porosity, opacity, bacteria content, combinations thereof, and the like.

As used herein, the term "sample," or variations thereof, refers to at least a portion of a substance of interest to be tested or otherwise evaluated using the optical computing devices described herein. The sample includes the characteristic of interest, as defined above, and may be any fluid, as defined herein, or otherwise any solid substance or material such as, but not limited to, rock formations, concrete, other solid surfaces, etc.

Conventional tungsten electromagnetic radiation source filaments are housed in large bulbs having sufficient surface area to minimize the thickness of deposited tungsten that builds up over the life span of the electromagnetic radiation source. In contrast, the tubular envelope in tungsten-halogen electromagnetic radiation sources is filled with an inert gas (either nitrogen, argon, krypton, or xenon) that is mixed during assembly with a minute amount of a halogen compound (usually hydrogen bromide; HBr) and trace levels of molecular oxygen. When power is applied to the electromagnetic radiation source, the filament temperature rises rapidly to its operating temperature (in the vicinity of 2500 to 3000° C.), a sequence of events that also heats the fill gas and the envelope. Eventually, the envelope achieves its stable operating temperature, which ranges from 400 to 1000° C., depending upon the electromagnetic radiation source parameters. The temperature differential between the filament and the envelope creates thermal gradients and convection currents in the fill gas. Once the envelope reaches a temperature of approximately 200 to 250° C. (depending on the nature and amount of halogen vapor), the halogen regenerative cycle begins. The halogen compound serves to initiate a reversible chemical reaction with tungsten evaporated from the filament to yield gaseous tungsten oxyhalide molecules in the vapor phase. Thermal gradients formed as a result of the temperature differential between the hot filament and the cooler envelope contribute to the interception and recycling of tungsten to the electromagnetic radiation source filament. Continuous recycling of metallic tungsten back and forth between the vapor phase and the filament maintains a more uniform wire thickness than would otherwise be possible.

The halogen regenerative cycle provides the ability to use small envelopes that are maintained in a clean, deposit-free condition during the life span of the electromagnetic radiation source. Because the envelope is smaller than those used in conventional tungsten electromagnetic radiation sources, expensive quartz and related glass alloys can be more economically employed during fabrication of present tungsten-halogen electromagnetic radiation sources. The quartz envelopes enable higher internal gas pressure to be used to assist in suppression of filament vaporization, thus allowing increased filament temperatures that produce more luminous output and shift optical emission profiles to feature a greater proportion of the more desirable visible wavelengths. As a result, tungsten-halogen electromagnetic radiation sources retain their original brightness throughout their life span and also convert electric current to electromagnetic radiation more efficiently than their predecessors. However, the tungsten vaporized and re-deposited by the halogen regenerative cycle is not necessarily returned to its original location, but rather winds up on the coolest regions of the filament, resulting in uneven thickness. Eventually the electromagnetic radiation sources fail due to decreased filament thickness in the hottest regions.

FIG. 1 shows a schematic representation of one example of a tungsten-halogen electromagnetic radiation source of the present disclosure. Tungsten-halogen electromagnetic radiation source 100 comprises a sealed transparent polycrystalline envelope 104 that defines an interior volume 105. Interior volume 105 may contain a fill gas 106 that comprises a halogen gas, for example, fluorine, bromine, and iodine. Tungsten filament 102 is located within the interior volume 105 of sealed polycrystalline envelope 104 and is attached by electrical leads 112 to power source 108. When energized, the filament 102 produces electromagnetic radiation 110, and the combination of the halogen gas and the tungsten filament produces a regenerative halogen cycle chemical reaction, which re-deposits evaporated tungsten back onto the filament. Continuous recycling of metallic tungsten back and forth between the vapor phase and the filament maintains a more uniform wire thickness than would otherwise be possible. The regenerative nature of the cycle provides increased life to the electromagnetic radiation source.

Figure 2:
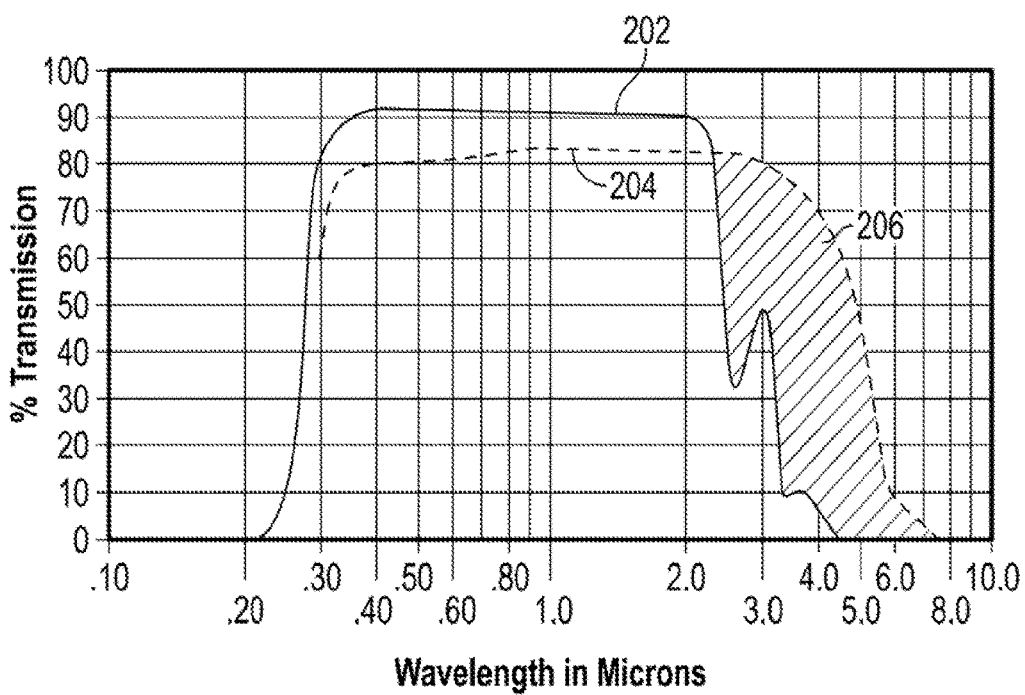
FIG. 2 is a diagram that shows the estimated increased spectral transmission of a tungsten-halogen electromagnetic radiation source having an aluminum oxynitride envelope compared to a tungsten-halogen electromagnetic radiation source having a quartz envelope.

In a specific embodiment, the polycrystalline transparent ceramic may include or be formed substantially from polycrystalline aluminum oxynitride (AlON). AlON is an isotropic material with a spinel crystal structure stabilized by incorporation of nitrogen into aluminum oxide. AlON has a general chemical formula of $Al_{23}O_{27}N_5$. AlON is substantially transparent to electromagnetic radiation with wavelengths from the ultraviolet to the mid-infrared range (10 nm to 5000 nm). FIG. 2 shows the estimated spectral transmission for AlON 204 compared to that of quartz 202, resulting in increased spectral transmission area 206. AlON exhibits low density, high strength, and high durability, and improved chemical resistance to gaseous halides, including fluorides. AlON may also generally be subjected to greater tension without breaking than quartz.

Referring again to FIG. 1, fill gas 106 may comprise a mixture of non-reactive gases, for example nitrogen, helium, neon, and argon, and at least one halogen gas compound 107. In certain embodiments, the at least one halogen gas compound may comprise a fluoride compound. The addition of fluoride compounds to the fill gas 106 may produce outputs with the highest level of visible wavelengths, increasing the range of color temperatures afforded by similar electromagnetic radiation sources having alternative halogen compounds (iodide, chloride, and bromide). Additionally, the use of fluoride compounds may lead to recycled tungsten being deposited on regions of the filament 102 with higher temperatures, thereby maintaining the filament 102 at a more uniform thickness during use and increasing the life span of the source.

Figure 3:
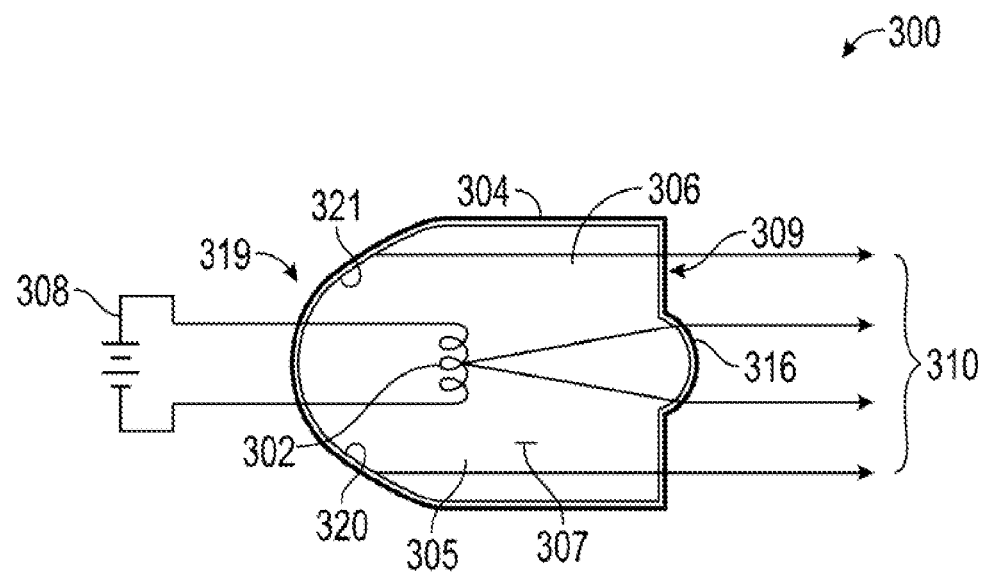
FIG. 3 shows another example of a tungsten-halogen electromagnetic radiation source having at least one integrally formed optical element formed in the tungsten-halogen electromagnetic radiation source envelope in accordance with aspects of the present disclosure.

Notably, fluoride compounds aggressively attack glass and quartz, which, when used with a typical source, may lead to a premature failure of the envelope. However, the enhanced chemical resistance of AlON allows the use, in the presently disclosed electromagnetic radiation source, of fluoride gases. The resulting electromagnetic radiation source has a longer life, a higher color temperature, and a broader optical bandwidth when compared to commonly available tungsten-halogen electromagnetic radiation sources. Fluoride compounds may include, but are not limited to, fluoroform ($CHF_3$), silver (II) fluoride ($AgF_2$), silver subfloride ($Ag_2F$) which decompose at bulb operating temperatures, FIG. 3 shows another example of a tungsten-halogen electromagnetic radiation source 300. Electromagnetic radiation source 300 comprises a sealed envelope 304 defining an interior volume 305, a tungsten filament 302, and a fill gas 306 that may include a fluoride compound 307. Electromagnetic radiation source 300 is fabricated from a transparent polycrystalline ceramic material, for example, an AlON material, as described previously. In one or more embodiments, electromagnetic radiation source 300 may also comprise at least one optical element integrally formed as part of the electromagnetic radiation source envelope 304.

Example integrally formed optical element include mirror shapes, lenses and light pipes (also called optical transmission rods). The formation of the integral optical element is facilitated by the polycrystalline nature of AlON, which allows it to be shaped into complex geometries during its casting process. Various casting techniques may be used to form AlON, for example, hot pressing and slip casting. Other conventional methods for forming polycrystalline materials from powder may also be used with AlON.

As shown in FIG. 3, the integrally formed optical element comprises a mirror 320 formed onto the exterior surface 319 of envelope 304 and a lens 316 formed in an opposite, front surface 309 of envelope 304. Mirror 320 may be a spherical or a parabolic shaped surface. Mirror 320 comprises a reflecting coating deposited on the curved exterior surface 319 to enhance the reflection of electromagnetic radiation emitted from filament 302. The combination of reflected and emitted electromagnetic radiation is transmitted through the front end 309 of envelope 304 as electromagnetic radiation 310. Lens 316 may be formed as a convex lens, a concave lens, or alternatively, as a Fresnel lens to assist in collecting and collimating the electromagnetic radiation 310 emitted by filament 302. Fresnel lenses are known in the optical arts and are not described here, in detail.

Figure 4:
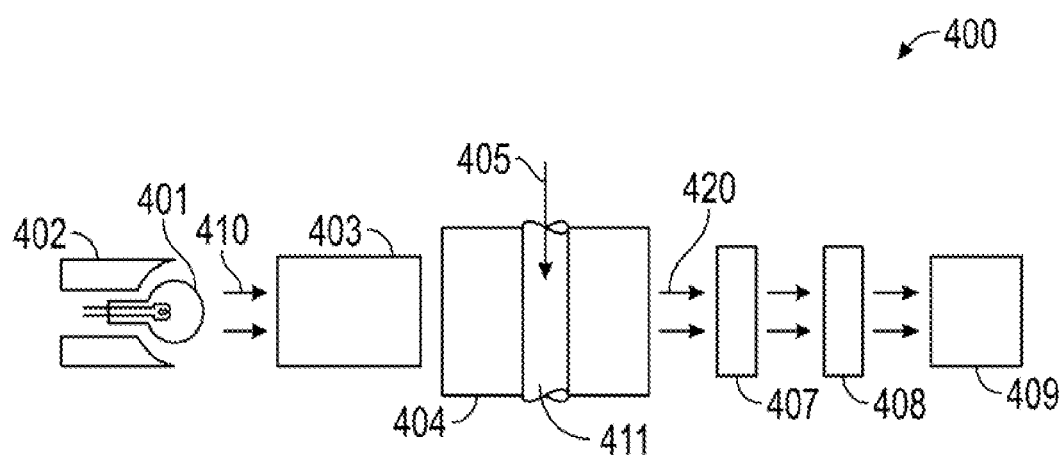
FIG. 4 shows an example of an optical system for making spectrometric measurements of a fluid sample in accordance with aspects of the present disclosure.

Other optical elements may also be integrally formed into an AlON electromagnetic radiation source The tungsten-halogen electromagnetic radiation source described above may be incorporated into an optical system that may be used to determine physical and/or chemical characteristics of fluid samples. FIG. 4 is one example of an optical system 400 incorporating a tungsten-halogen electromagnetic radiation source, as described above, with a polycrystalline envelope. Tungsten-halogen electromagnetic radiation source 401 is supported by reflector 402. Electromagnetic radiation 410 from electromagnetic radiation source 401 is transmitted into an optical light pipe 403 (also called an optical coupling rod), and then into an optically transparent sample block 404 that has a passage 411 therethrough. The passage 411 may be in fluid communication with a fluid sample 405, which may pass through passage 411. As the fluid sample 405 passes through the block 404, it may interact with the electromagnetic radiation 410 also traveling through the block 404, resulting in a sample interacted electromagnetic radiation 420. Sample interacted electromagnetic radiation 420 may be transmitted radiation or reflected radiation. Sample interacted electromagnetic radiation 420 may then be processed by optical computing device 407 resulting in processed electromagnetic radiation. Processed electromagnetic radiation is focused by lens 408 onto and detected by optical transducer 409.

Figure 5:
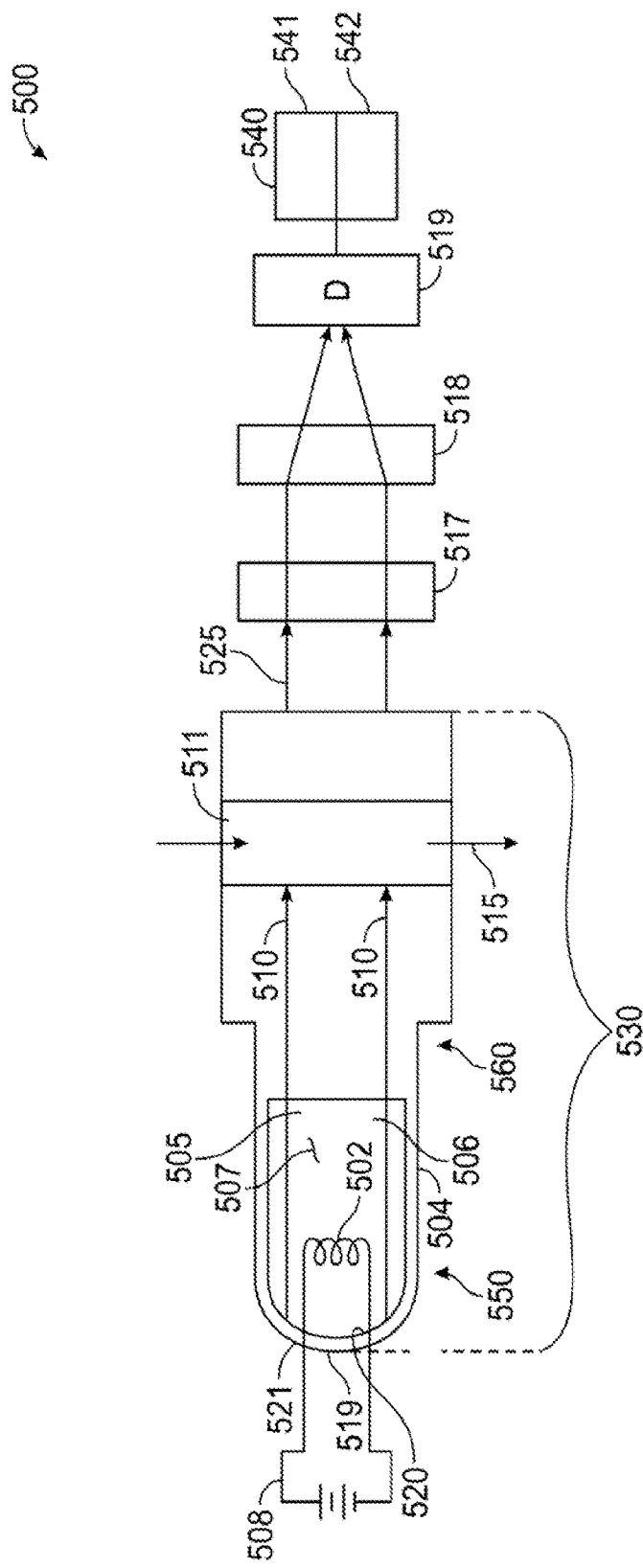
FIG. 5 shows an example of a optical system incorporating a tungsten-halogen electromagnetic radiation source having at least one integrally formed optical element formed in the tungsten-halogen electromagnetic radiation source envelope in accordance with aspects of the present disclosure.

FIG. 5 shows another optical system 500 wherein a number of components, for example from FIG. 4, are formed into an integral sample assembly 530. The use of integral AlON components can improve optical throughput, and increase signal-to-noise ratio (SNR), in optical systems by combining multiple optical elements into fewer optical elements. This increase in SNR may be accomplished by eliminating some optical interfaces, which cause reflection losses. In the example shown, sample assembly 530 comprises a tungsten-halogen electromagnetic radiation source 550, an optical coupling element, also called a waveguide, 560, and a transparent sample block 510 formed as a single element from a polycrystalline AlON material, as described previously. Tungsten-halogen electromagnetic radiation source 550 comprises an AlON envelope 504 formed to define an internal cavity 505. A tungsten filament 502 is located in cavity 505 and is connected through electrical leads to an electrical power source 508. Cavity 505 has a fill gas 506 therein, where the fill gas 506 comprises at least a halogen gas 507. In one example the halogen gas comprises a gaseous fluoride compound, as described previously. When energized, filament 502 produces electromagnetic radiation, and the combination of the halogen gas 507 and tungsten filament 502 produces a regenerative halogen cycle electromagnetic radiation source, emitting an electromagnetic spectrum as described above. Electromagnetic radiation source 550 may have a mirror 520 formed into exterior surface 519. Mirror 520 may be a spherical or a parabolic shaped surface. Mirror 520 may comprise a reflecting coating 521 deposited on the curved exterior surface 519 to enhance the reflection of electromagnetic radiation emitted from filament 502. The electromagnetic radiation 510 from electromagnetic radiation source 550 is transmitted through optical coupling element 560 and passes through, and interacts with, a fluid sample 515 located within a sample passage 511 in sample block 570 resulting in a sample interacted electromagnetic radiation 525. Sample interacted electromagnetic radiation 525 may be transmitted radiation or reflected radiation. Sample interacted electromagnetic radiation 525 may then be processed by optical computing device 517 and focused by a lens 518 and then be detected at an optical transducer 519. The detected signal may be used to determine at least one characteristic of the sample fluid 515. In one example, optical transducer 519 is in data communication with a controller 540. Controller 540 may comprise at least one processor 541 in data communication with a memory 542. Memory 542 may contain programmed instructions that, when executed by the processor 541, cause the processor to 541 determine at least one characteristic of sample fluid 515.

Figure 6:
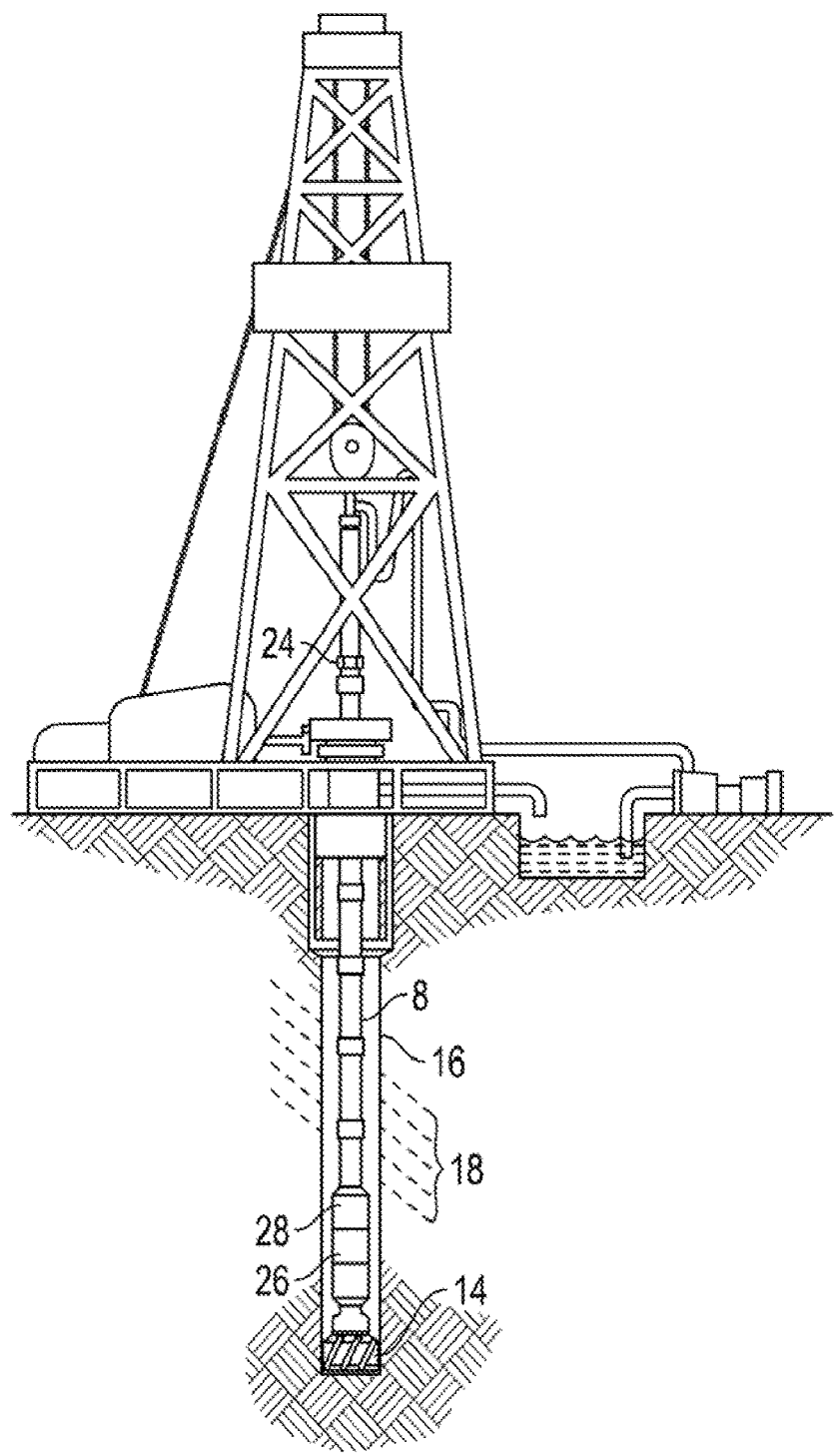
FIG. 6 shows an example of a logging while drilling system in accordance with aspects of the present disclosure.

In another example embodiment, as shown in FIG. 6, a logging tool 26 containing a tungsten-halogen polycrystalline transparent ceramic electromagnetic radiation source 100, 300 and/or an optical system 400, 500, as described in any of the embodiments above, may be integrated into a bottom-hole assembly 50 near a drill bit 14 located in a borehole 16. In other embodiments, the logging tool 26 may be located at any point along the drill string 8. The logging tool 26 may include receivers and/or transmitters (e.g., antennas capable of receiving and/or transmitting one or more electromagnetic signals). In some embodiments, the logging tool 26 may include a transceiver array that functions as both a transmitter and a receiver. As the bit extends the borehole 16 through the subterranean formations 18, the logging tool 26 may collect measurements relating to various formation properties as well as the tool orientation and position and various other drilling conditions. The orientation measurements may be performed using an azimuthal orientation indicator, which may include magnetometers, inclinometers, and/or accelerometers, though other sensor types such as gyroscopes may be used in some embodiments. In embodiments including an azimuthal orientation indicator, resistivity and/or dielectric constant measurements may be associated with a particular azimuthal orientation (e.g., by azimuthal binning) A telemetry hub 28 may be included to transfer tool measurements to a surface receiver 24 or to receive commands from the surface receiver 24.

Figure 7:
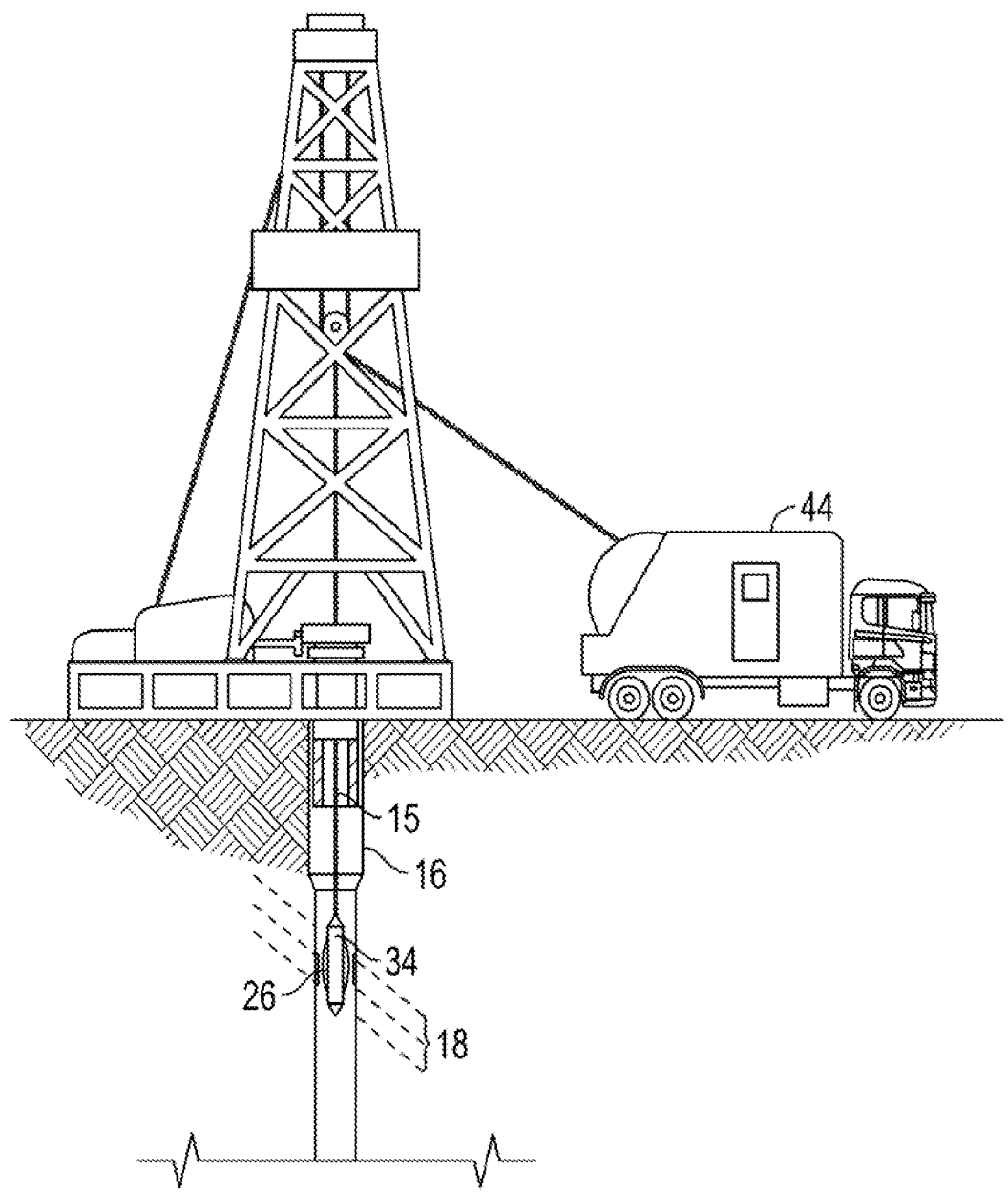
FIG. 7 shows an example of a wireline logging system in accordance with aspects of the present disclosure.

At various times during the drilling process, the drill string 8 may be removed from the borehole 16. Once the drill string has been removed, logging operations can be conducted using a wireline logging system 34, see FIG. 7. The wireline system 34 may include one or more logging sensors or tools 26 containing a tungsten-halogen polycrystalline transparent ceramic electromagnetic radiation source 100, 300 and/or an optical system 400, 500, according to the present disclosure. The logging sensor or tool 26 may be communicatively coupled to the cable 15. A logging facility 44 (shown in FIG. 7 as a truck, although it may be any other structure) may collect measurements from the logging sensor or tool 26, and may include computing facilities 43 for controlling, processing, or storing the measurements gathered by the logging sensor or tool 26. The computing facilities may communicate with the logging sensor, or tool, 26 by way of the cable 15.

Figure 8:
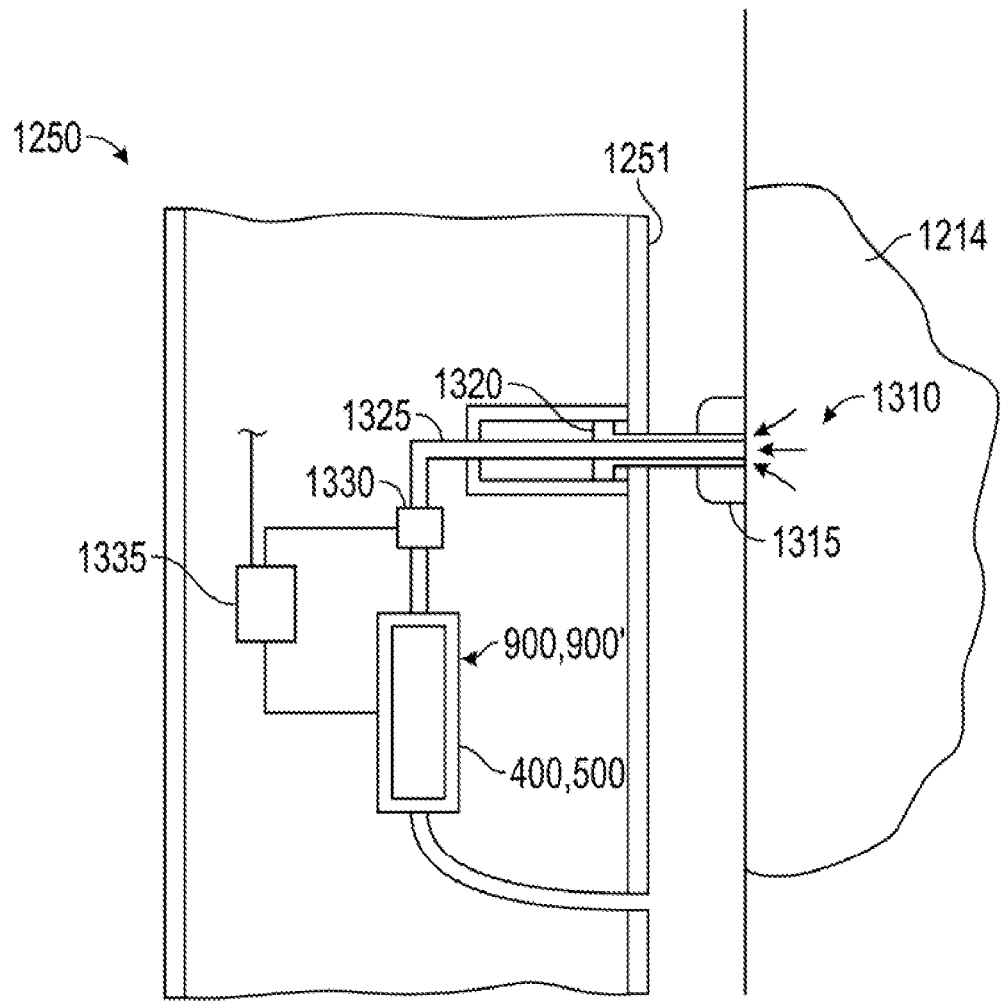
FIG. 8 shows an example of a testing tool for testing a formation sample in accordance with aspects of the present disclosure.

FIG. 8 shows an example of a portion of a logging tool 1250 for extracting and testing a fluid sample downhole. Such a tool may be conveyed into a wellbore using at least one of a drill string, a logging cable, and any other suitable conveyance system. Probe 1315 may be extended from tool body 1251 by piston 1320 of tool 1250 and contacts wall 1213 of wellbore 1212. In one embodiment, the suction side of pump 1330 is in fluid communication with formation 1214 through flow passage 1325 that extends through piston 1320 and probe 1315. Activation of pump 1330 extracts a fluid sample 1310 from formation 1214. Fluid sample 1310 may comprise a liquid, a gas, solids, and combinations thereof. Fluid sample 1310 may be forced through optical system 400, 500 located in testing tool 1250 for detecting one or more parameters related to fluid sample 1310. In one example, optical system 400, 500 is in data communication with controller 1335 of testing tool 1250. Controller 1335 may contain circuits and a processor with memory for controlling the operation of testing tool 1250.

Data from analyses of formation fluids performed by logging sensor or tool 26 may be used to control the operation of at least some of the drilling equipment. In such specific embodiments, fluids may be extracted either from the formation or the bore hole and pumped through a series of sensors within the logging sensor or tool 26. These sensors may characterize the fluids' physical properties, such as density, viscosity, phases (gas, liquid, slurry, etc.), electrical properties, impedance, resistivity, and capacitance. The composition may also be determined using optical sensors. The tool set may also allow capture of the fluid downhole, which may later be analyzed at the surface. For downhole tools, the data from optical sensors may be transmitted to the surface by telemetry through wires, acoustical pulses into the mud, or electromagnetic pulses. In many cases, the data may be stored with in the tool set so a more complete record of observation may be recovered once the tool set has returned to surface.

Although only exemplary embodiments of the invention are specifically described above, it will be appreciated that modifications and variations of these examples are possible without departing from the spirit and intended scope of the invention.

The invention claimed is:

1. A tungsten-halogen electromagnetic radiation source, comprising:
a sealed transparent polycrystalline ceramic envelope defining an interior volume;
a tungsten filament disposed within the interior volume; and
a fill gas in the interior volume wherein the fill gas contains at least a gaseous halogen compound;
wherein the transparent polycrystalline ceramic envelope is made from an aluminum oxynitride material.

2. The tungsten-halogen electromagnetic radiation source of claim 1 wherein the transparent polycrystalline ceramic envelope further comprises at least one optical element integrally formed into the envelope.

3. The tungsten-halogen electromagnetic radiation source of claim 2 wherein the at least one optical element integrally formed into the envelope is chosen from the group consisting of: an optical mirror, an optical lens, and an optical electromagnetic radiation guide.

4. The tungsten-halogen electromagnetic radiation source of claim 3 wherein the optical mirror is chosen from the group consisting of: a spherical mirror and a parabolic mirror.

5. The tungsten-halogen electromagnetic radiation source of claim 3 wherein the optical lens is chosen from the group consisting of: a convex lens, a concave lens and a Fresnel lens.

6. The tungsten-halogen electromagnetic radiation source of claim 3 wherein the optical mirror further comprises a reflective coating deposited thereon.

7. The tungsten-halogen electromagnetic radiation source of claim 1, wherein the gaseous halogen compound comprises a fluoride compound.

8. The tungsten-halogen electromagnetic radiation source of claim 7 wherein the fluoride compound is chosen from the group consisting of: a fluoroform (CHF3, a silver (II) fluoride (AgF2), and a silver subfloride (Ag2F) compound.

9. A system for detecting at least one characteristic of a reservoir sample comprising:
a flow conduit;
an electromagnetic radiation source having a tungsten filament and a sealed optically transparent aluminum oxynitride envelope, the sealed optically transparent envelope defining an interior volume;
an integrated computational optical element positioned opposite the flow conduit from the radiation source to receive a sample interacted electromagnetic radiation from the electromagnetic radiation source;
a radiation transducer positioned to receive the sample interacted electromagnetic radiation from the integrated computational optical element.

10. The system of claim 9 further comprising a fill gas in the interior volume of the electromagnetic radiation source wherein the fill gas contains at least one gaseous fluoride compound chosen from the group consisting of: a fluoroform (CHF3) compound, a silver (II) fluoride (AgF2) compound, and a silver subfloride (Ag2F) compound.

11. The system of claim 9 wherein the sealed optically transparent envelope of the electromagnetic radiation source further comprises at least one optical element integrally formed into the sealed optically transparent envelope.

12. The system of claim 11 wherein the at least one optical element integrally formed into the sealed optically transparent envelope is chosen from the group consisting of: an optical mirror, an optical lens, and an optical electromagnetic radiation guide.

13. The system of claim 12 wherein the optical mirror is chosen from the group consisting of: a spherical mirror and a parabolic mirror.

14. The system of claim 12 wherein the optical lens is chosen from the group consisting of: a convex lens, concave lens, and a Fresnel lens.

15. The system of claim 9 further comprising a controller to relate an output signal from the radiation transducer to at least one characteristic of the reservoir sample.

16. A tungsten-halogen electromagnetic radiation source, comprising:
a sealed transparent aluminum oxynitride envelope defining an interior volume;

at least one optical element integrally formed into the aluminum oxynitride envelope;
a tungsten filament; and
a fill gas in the interior volume wherein the fill gas contains at least a gaseous fluoride compound.

17. The tungsten-halogen electromagnetic radiation source of claim 16 wherein the at least one optical element integrally formed into the aluminum oxynitride envelope is chosen from the group consisting of: an optical mirror, an optical lens, and an optical electromagnetic radiation guide.

18. The tungsten-halogen electromagnetic radiation source of claim 17 wherein the optical mirror is chosen from the group consisting of: a spherical mirror and a parabolic mirror.

19. The tungsten-halogen electromagnetic radiation source of claim 17 wherein the optical lens is chosen from the group consisting of: a convex lens; a concave lens, and a Fresnel lens.

20. The tungsten-halogen electromagnetic radiation source of claim 16 wherein the gaseous fluoride compound is chosen from the group consisting of: a fluoroform ($CHF_3$) compound, a silver (II) fluoride ($AgF_2$) compound, and a silver subfloride ($Ag_2F$) compound.

* * * * *